US008219419B1

(12) United States Patent
Fava et al.

(10) Patent No.: US 8,219,419 B1
(45) Date of Patent: *Jul. 10, 2012

(54) SYSTEM AND METHOD FOR REDUCING THE PLACEBO EFFECT IN CONTROLLED CLINICAL TRIALS

(75) Inventors: Maurizio Fava, Newton, MA (US); David Schoenfeld, Sharon, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/403,060

(22) Filed: Feb. 23, 2012

Related U.S. Application Data

(63) Continuation of application No. 13/176,091, filed on Jul. 5, 2011, now Pat. No. 8,145,505, which is a continuation of application No. 13/156,481, filed on Jun. 9, 2011, now Pat. No. 8,145,504, which is a continuation of application No. 12/909,075, filed on Oct. 21, 2010, now Pat. No. 7,983,936, which is a continuation of application No. 12/545,562, filed on Aug. 21, 2009, now Pat. No. 7,840,419, which is a continuation of application No. 10/814,852, filed on Mar. 31, 2004, now Pat. No. 7,647,235.

(60) Provisional application No. 60/459,517, filed on Mar. 31, 2003.

(51) Int. Cl.
| | |
|---|---|
| G06Q 10/00 | (2006.01) |
| G06Q 50/00 | (2006.01) |
| A61B 5/00 | (2006.01) |
| G06F 19/00 | (2006.01) |

(52) U.S. Cl. ..................... 705/2; 705/1; 705/3
(58) Field of Classification Search .......... None
See application file for complete search history.

(56) References Cited

U.S. PATENT DOCUMENTS 5,898,586 A    4/1999 Jeatran et al.
(Continued)

FOREIGN PATENT DOCUMENTS

WO    WO 01/32017 A2    5/2001
(Continued)

OTHER PUBLICATIONS

"Effect of Hypericum Perforatum (St. John's Wort) in Major Depressive Disorder—A Randomized Controlled Trial;" Journal of the American Medical Association; vol. 287, No. 14; Apr. 2002; pp. 1807-1814.

(Continued)

Primary Examiner — Robert Morgan
Assistant Examiner — Eliza Lam
(74) Attorney, Agent, or Firm — Daly, Crowley, Mofford & Durkee, LLP

(57) ABSTRACT

A method and system for performing a clinical trial having a reduced placebo effect is disclosed. The method includes randomizing study participants into three or more treatment groups and performing a first phase of testing on the groups. In a typical embodiment, the first phase of testing includes administering an active treatment to a first group, and administering a placebo to a second group and to a third group. Responders and non-responders are determined for each group. A second phase of testing is then performed. The second phase of testing includes administering the placebo to non-responders in the first group, administering the active treatment to non-responders in the second group, and administering the placebo to non-responders in the third group. The data from the first phase of testing and from the second phase of testing is pooled and analyzed to determine response rates to active treatment and placebo.

8 Claims, 5 Drawing Sheets

U.S. PATENT DOCUMENTS

| | | | |
|---|---|---|---|
| 5,991,731 | A | 11/1999 | Colon et al. |
| 6,041,788 | A | 3/2000 | Shen |
| 6,450,954 | B1 | 9/2002 | Selker |
| 7,647,235 | B1 | 1/2010 | Fava et al. |
| 7,840,419 | B1 | 11/2010 | Fava et al. |
| 7,983,936 | B1 | 7/2011 | Fava et al. |
| 2002/0143563 | A1 | 10/2002 | Hufford et al. |

FOREIGN PATENT DOCUMENTS

| | | | |
|---|---|---|---|
| WO | WO 01/32071 | A2 | 5/2001 |
| WO | WO 01/32071 | A3 | 5/2001 |

OTHER PUBLICATIONS

Bech et al.; "The Hamilton Depression Scale, Evaluation of Objectivity Using Logistic Models;" Acta Psychiat. Scand. (1981) 63; 1981; pp. 290-299.

Campbell et al.; "A Primer on Regression Artifacts;" The Guilford Press; New York; 1999; entire book.

Chassan; "Intensive Design: Statistics and the Single Case;" Research Designs and Methods in Psychiatry; Chapter 11; Jan. 1992; pp. 173-183.

Chmura Kraemer et al.; "Methodology in Psychiatric Research;" Archives of General Psychiatry; vol. 44; Dec. 1987; pp. 1100-1106.

Cutter et al.; "Development of a Multiple Sclerosis Functional Composite as a Clinical Trial Outcome Measure;" Brain, vol. 122; 1999; pp. 871-882.

DeBrota et al.; "Same Rater Versus Different Raters in Depression Clinical Trials;" $42^{nd}$ Annual NCDUE Meeting; Boca Raton, FL; Jun. 10, 2000; 1 sheet.

Demitrack et al; "The Problem of Measurement Error in Multisite Clinical Trials;" Psychopharmacology Bulletin 34 (1); 1998; pp. 19-24.

Diener et al.; "Cyclandelate in the Prophylaxis of Migraine: A Randomized Parallel, Double-Blind Study in Comparison with a Placebo and Propranolol;" Cephalalgia; 1996; pp. 16:441-447.

Dunger-Baldauf, et al.; "Designs with Randomization Following Initial Study Treatment" Wiley Enclopedia of Clinical Trials, copyright 2007; pp. 1-7.

Dunger-Baldauf, et al.; "Re-Treatment Studies: Design and Analysis;" Drug Information Journal, vol. 40; 2006; pp. 209-217.

Faries et al.: "The Double-Blind Variable Placebo Lead-in Period: Results From Two Antidepressant Clinical Trials;" Journal of Clinical Psychopharmacology; vol. 21, No. 6; Dec. 2001; pp. 561-568.

Faries et al.; "The Responsiveness of the Hamilton Depression Rating Scale;" Journal of Psychiatric Research; vol. 34, Jan. 2000; pp. 3-10.

Fava et al.; "The Problem of the Placebo Response in Clinical Trials for Psychiatric Disorders: Culprits, Possible Remedies, and a Novel Study Design Approach;" Psychotherapy and Psychosomatics; May/Jun. 2003; pp. 72:15-127.

Fava et al.; "How to Write a Study Protocol: A Primer for the Clinician;" Research Designs and Methods in Psychiatry; Ch. 20, Jan. 1992; pp. 297-305.

Fava et al.; "Major Depressive Subtypes and Treatment Response;"1997 Society of Biological Psychiatry; vol. 42; Jan. 1997; pp. 568-576.

Fava; "Traditional and Alternative Research Designs and Methods in Clinical Pediatric Psychopharmacology;" Journal of the American Academy of Child Adolescent Psychiatry; vol. 34, No. 10; Oct. 1996; pp. 1292-1303.

Fiore et al.; "The Effectiveness of the Nicotine Patch for Smoking Cessation: A Meta-analysis;" 9 pages as printed in the Journal of the American Medical Association; Jun. 22, 1994; pp. 1940-1947.

Gibbons et al.; "Exactly What Does the Hamilton Depression Rating Scale Measure?;" Journal of Psychiatric Research; vol. 27, No. 3; Jan. 1993; pp. 259-273.

Hooper et al.; "Do Clinical Trials Reflect Drug Potential: A Review of 5 FDA Evaluations of New Antidepressants;" $39^{th}$ Annual NCDUE Meeting; Boca Raton, FL; Jun. 11-14, 1998; Poster No. 182, 1 sheet.

Hróbjartsson et al.; "Is the Placebo Powerless? Update of a Systematic Review With 52 New Randomized Trials Comparing Placebo With No Treatment;" Journal of Internal Medicine; vol. 256; Jan. 2004; pp. 91-100.

Jorenby et al.; "A Controlled Trial of Sustained-Release Bupropion, A Nicotine Patch, or Both for Smoking Cessation;" New England Journal of Medicine; vol. 340, No. 9; Jan. 1999; pp. 685-691.

Kellner; "The Development of Sensitive Scales for Research in Therapeutics;" Research Designs and Methods in Psychiatry; Jan. 1992; pp. 213-222.

Kobak et al.; "Computerized Assessment of Depression and Anxiety Over the Telephone Using Interactive Voice Response;" MD Computing; vol. 16; May 1999; pp. 64-68.

Koch et al.; "Methodological Advances and Plans for Improving Regulatory Success for Confirmatory Studies;" Statistics in Medicine, vol. 17; 1998; pp. 1675-1690.

Laird; "Estimating Rates of Change in Clinical Studies;" Research Designs and Methods in Psychiatry; Chapter 12; Jan. 1992; pp. 185-193.

Lin; "An Issue of Statistical Analysis in Controlled Multi-Centre Studies: How Shall We Weight the Centres?;" Statistics in Medicine, vol. 18; 1999; pp. 365-373.

Myers et al.; Information, Compliance and Side-Effects: A Study of Patients on Antidepressant Medication; British Journal of Clinical Pharmacology; vol. 17(1); Jan. 1984; pp. 21-25.

NDA; Center for Drug Evaluation and Research, Application No. 18-936/S-036; Food and Drug Administration; 1988.

Niaura et al.; "Multicenter Trial of Fluoxetine as an Adjunct to Behavioral Smoking Cessation Treatment;" Journal of Consulting and Clinical Psychology; vol. 70, No. 4; Feb. 2002; pp. 887-896.

O'Sullivan et al.; "Sensitivity of the Six-Item Hamilton Depression Rating Scale;" American College of Rheumatology Psychiatric Scandinavian; vol. 95; Jan. 1997; pp. 379-384.

Otto et al.; "Assay Sensitivity, Failed Clinical Trials, and the Conduct of Science;" 9 pages as printed in Psychotherapy Psychosomatics; Jan. 2002; vol. 71; pp. 241-243.

Peselow et al.; "Melancholic/Endogenous Depression and Response to Somatic Treatment and Placebo;" American Journal of Psychiatry; vol. 149, No. 10; Oct. 1992; pp. 1324-1334.

Quitkin et al.; "Are There Differences Between Women's and Men's Antidepressant Responses?:" American Journal of Psychiatry; vol. 159, No. 11; Nov. 2002; pp. 1848-1854.

Quitkin et al.; "Identification of True Drug Response to Antidepressants;" Archives of General Psychiatry; vol. 41; Aug. 1984; pp. 782-786.

Quitkin; "Methodology of Measuring the Efficacy of Antidepressants;" Psychopharmacology (Berl); vol. 106; Jan. 1992; pp. S87-S89.

Rao et al.: "Linear Statistical Inference and its Applications;" New York: Wiley; 1952, p. 50.

Reginster et al.; "Long-Term Effects of Glucosamine Sulphate on Osteoarthritis Progression: A Randomised, Placebo-Controlled Clinical Trial;" The Lancet, vol. 357, Issue 9252; Jan. 27, 2001; pp. 251-256.

Robinson et al.; "Concerns About clinical Drug Trials;" Journal of Clinical Psychopharmacology; Dec. 2000; vol. 20, No. 6; pp. 593-596.

Rush et al.; "The Inventory of Depressive Symptomatology (IDS): Clinician (IDS-C) and Self-Report (IDS-SR) Ratings of Depressing Symptoms;" International Journal of Methods in Psychiatric Research; vol. 9, No. 2; Jan. 2000; pp. 49-59.

Schatzbert et al.; "Use of Placebo Control Groups in Evaluating Efficacy of Treatment of Unipolar Major Depression;" 2000 Society of Biological Psychiatry; Jan. 2000; vol. 47; pp. 736-744.

Shelton et al.; "Effectiveness of St. John's Wort in Major Depression—A Randomized Controlled Trial;" Journal of the American Medical Association; vol. 285, No. 15; Apr. 2001; pp. 1978-1986.

Shiffman et al.; "A Randomized Controlled Trial of Maintenance Interferon Therapy for Patients with Chronic Hepatitis C Virus and Persistent Viremia;" Gastroenterology; Nov. 1999; vol. 117, No. 5; pp. 1164-1172.

Shun et al.; "Statistical Consideration of the Strategy for Demonstrating Clinical Evidence of Effectiveness—One Larger vs. Two Smaller Pivotal Studies;" Statistics of Medicine; 2005; pp. 24: 1639-1651.

Simpson et al.; "Two Dosages of Imipramine in Hospitalized Endogenous and Neurotic Depressives;" Archives of General Psychiatry; vol. 33; Sep. 1976; pp. 1093-1103.

Stevens et al.; "A Randomized Trial of Itraconazole in Allergic Bronchopulmonary Aspergillosis;" The New England Journal of Medicine; Mar. 16, 2000; pp. 756-881.

Trivedi et al.; "Does a Placebo Run-In or a Placebo Treatment Cell Affect the Efficacy of Antidepressant Medications?;" American College of Neuropsychopharmacology 1994; vol. 11, No. 1; Mar. 1994; pp. 33-43.

Uhlenhuth et al.; "Intensive Design in Evaluating Anxiolytic Agents;" Psychopharmacology; vol. 52; Jan. 1977; pp. 79-85.

Walsh et al.; "Placebo Response in Studies of Major Depression: Variable, Substantial, and Growing;" Journal of the American Medical Association; vol. 287, No. 14; Apr. 10, 2002; pp. 1840-1847.

Brown, Jr.; "The Crossover Experiment for Clinical Trials;" Publication of Stanford University Medical Center, Stanford, CA; Biometrics 36; Mar. 1980; pp. 69-79.

Carriere; "Crossover Designs for Clinical Trials;" Statistics in Medicine; vol. 13; Apr. 1993; pp. 1063-1069.

Farlow et al.; "A 52-Week Study of the Efficacy of Rivastigmine in Patients with Mild to Moderately Sever Alzheimer's Disease;" European Neurology; vol. 4, Nov. 2000; pp. 236-241.

Hills et al.; "The Two-Period Cross-Over Clinical Trial;" British Journal of Clinical Pharmacology; Jul. 1979; pp. 7-20.

Leber et al.; "Threats to the Validity of Clinical Trials Employing Enrichment Strategies for Sample Selection;" Elsevier Science Inc.; Controlled Clinical Trials; vol. 19, Issue 2 Apr. 1998; pp. 178-187.

Raskind et al; "Galantamine in AD: A 6-month randomized, placebo-controlled trial with a 6-month extension;" American Academy of Neurology; Jun. 2000; pp. 2260-2269.

Rosner et al; "Randomized Discontinuation Design: Application to Cytostatic Antineoplastic Agents;" Journal of Clinical Oncology; vol. 20, No. 22; Nov. 15, 2002; pp. 4478-4484.

Temple; "Special Study Designs: Early Escape, Enrichment, Studies in Non-Responders;" Communications in Statistics-Theory and Method; vol. 23, Issue 2; 1994; pp. 499-531.

Klein et al.; "Improving Clinical Trials" American Society of Clinical Psychopharmacology Recommendations, Arch Gen Psychiatry/vol. 59, Mar. 2002, pp. 272-278.

Doody et al.; "Open-Label, Multicenter, Phase 3 Extension Study of the Safety and Efficacy of Donepezil in Patients With Alzheimer Disease", Arch Neurol/vol. 58, Mar. 2001, pp. 427-433.

Grandi; "The Sequential Parallel Comparison Model: A Revolution in the Design of Clinical Trials", Affective Disorders Program, Department of Psychology, University of Bologna, Bologna, Italy, Psychotherapy and Psychosomatics 2003; 72:113-114.

Laughren; "The scientific and ethical basis for placebo-controlled trials in depression and schizophrenia: an FDA perspective", Eur Psychiatry 2001; 16: 418-23.

Holbrook et al.; "Innovation and placebos in research: a new design of clinical trial", The Lancet, vol. 362, Dec. 20/27, 2003, pp. 2036-2037.

Koch et al.; "A Two-Period Crossover Design for the Comparison of Two Active Treatments and Placebo", Statistics in Medicine, vol. 8, 487-504 (1989).

Noseworthy et al.; "The impact of blinding on the results of a randomized, placebo-controlled multiple sclerosis clinical trial" American Academy of Neurology, 1994; 44; 16-20.

Streiner; "Placebo-controlled trials: when are they needed?" Schizophrenia Research 35 (1999), 201-210.

Talbot; "The Placebo Prescription", *New York Times Magazine*, Jan. 9, 2000, 10 pages.

Hrobjartsson et al.; "Is the placebo powerless? Update of a systematic review with 52 new randomized trials comparing placebo with no treatment", Journal of Internal Medicine 2004; 256:91-100.

Hart; "The mysterious placebo effect", Modern Drug Discovery, Jul./Aug. 1999, 2 (4) 30-40, 7 pages.

Faraone et al.; "The Drug-Placebo Response Curve: A New Method for Assessing Drug Effects in Clinical Trials", Journal of Clinical Psychopharmacology: Dec. 2000—vol. 20—Issue 6—pp. 673-679.

Nordenberg; "The Healing Power of Placebos", The Body, *FDA Consumer*, Jan./Feb. 2000, 6 pages.

Zelen; "A New Design for Randomized Clinical Trials", The New England Journal of Medicine, vol. 300, No. 22, May 31, 1979, pp. 1242-1245.

Hrobjartsson et al; "Is the Placebo Powerless? An Analysis of Clinical Trials Comparing Placebo with No Treatment", The New England Journal of Medicine, vol. 344, No. 21, May 24, 2001, pp. 1594-1603.

Ellenberg; "Randomization Designs in Comparative Clinical Trials", The New England Journal of Medicine, vol. 310, No. 21, May 24, 1984, 1404-1408.

Beller et al.; "Randomisation in clinical trials", MJA, vol. 177, Nov. 18, 2002, 565-567.

Altman et al.; "*Statistics notes* How to randomize", BMJ, vol. 319, Sep. 11, 1999, 703-704.

Hofmann, et al.., Prospective Randomized Trial to Evaluate Two Delayed Granulocyte Colony Stimulating Factor Administration Schedules After High-Dose Cytarabine Therapy in Adult Patients With Acute Lymphoblastic Leukemia , Ann Hemotol 81; Oct. 17, 2002, pp. 570-574.

Kraemer, Ph.D., et al., How Do Risk Factors Work Together? Mediators, Moderators, and Independent Overlapping and Proxy Risk Factors, American Journal of Psychiatry, Jun. 2001, pp. 848-856.

Kravitz, et al., Evidence-Based Medicine, Heterogeneity of Treatment Effects, and the Trouble with Averages, University of California, The Milbank Quarterly, vol. 82, No. 4, 2004, pp. 661-687.

William J. Carpenter, Jr., M.D., From Clinical Trial to Prescription, Arch Gen Psychiatry, vol. 59, Mar. 2002, pp. 282-285.

Kraemer, Ph.D., et al., Mediators and Moderators of Treatment Effects in Randomized Clinical Trials, Arch Gen Psychiatry, vol. 59, Oct. 2002, pp. 877-883.

U.S. Appl. No. 13/156,481, filed Jun. 9, 2011.

U.S. Appl. No. 13/176,091, filed Jul. 5, 2011.

SYSTEM AND METHOD FOR REDUCING THE PLACEBO EFFECT IN CONTROLLED CLINICAL TRIALS

CROSS REFERENCE TO RELATED APPLICATIONS

This application is a continuation application of U.S. patent application Ser. No. 13/176,091 filed on Jul. 5, 2011 now U.S. Pat. No. 8,145,505 which is a continuation of application Ser. No. 13/156,481 filed on Jun. 9, 2011 now U.S. Pat. No. 8,145,504 which is a continuation of U.S. patent application Ser. No. 12/909,075 filed on Oct. 21, 2010 now U.S. Pat. No. 7,983,936; which is a continuation of patent application Ser. No. 12/545,562 filed on Aug. 21, 2009 now U.S. Pat. No. 7,840,419; which is a continuation of patent application Ser. No. 10/814,852 filed on Mar. 31, 2004 now U.S. Pat. No. 7,647,235, which claims the benefit of provisional patent application No. 60/459,517 filed Mar. 31, 2003; which applications are hereby incorporated herein by reference in the entirety.

STATEMENT REGARDING FEDERALLY SPONSORED RESEARCH

Not Applicable

FIELD OF THE INVENTION

The present invention relates generally to clinical trials and more specifically to a method and apparatus for reducing the placebo effect and sample size requirements in such clinical trials.

BACKGROUND OF THE INVENTION

As is known in the medical field, the term "clinical drug treatment study" or "clinical drug trial" (or more simply a "clinical trial"), refers to the testing done on humans to determine the value of a given drug treatment. A clinical drug trial is referred to as a "controlled drug trial" when the effect of a drug treatment is measured against a comparison treatment or treatments administered over the same time period and under similar conditions. In the most typical form of controlled clinical trial, the comparison treatment is provided by supplying a placebo to test study participants in place of the actual treatment (placebo-controlled clinical trial).

As is also known, the term "blinding" in a clinical drug trial refers to the concealment of treatment assignment in order to prevent influencing the behavior, observation or reporting of the person receiving the treatments or of the person administering the treatment. In a double blind, clinical drug trial, both the persons receiving the treatment and the persons administering the treatment are unaware of which study participants are receiving which treatments.

As is also known, the term "randomization" in a clinical drug trial refers to the random assignment to treatment, so that a random sequence determines whether a given subject is assigned to active treatment(s) or placebo. Randomization is an important aspect of a clinical trial in that it eliminates possible biases in treatment assignment.

The purpose of a randomized, double-blind, placebo-controlled trial is to compare the efficacy of a specific treatment or treatments with that of placebo for study participants identified according to a priori criteria and assigned by chance to a given treatment group. The conventional design of such a trial involves the parallel comparison of one or more treatments with placebo, with sample sizes considered adequate to detect a therapeutic signal, given the expected placebo response rates in that specific population. As the term is commonly used, "placebo response" represents an apparent improvement in the clinical condition of study participants randomly assigned to the placebo treatment, (e.g., a pre-post treatment change within the placebo group). It is not uncommon for clinical trials to yield uninterpretable results, due in part to the placebo response. It has been suggested that addressing the placebo response issue is one of the most important challenges facing the future of industry-sponsored psychopharmacologic drug development.

SUMMARY OF THE INVENTION

In accordance with the present invention, a method of performing a clinical trial having a reduced placebo effect is disclosed. In one typical form, the method includes randomizing study participants into three treatment groups and performing a first phase of testing on the three groups. The first phase of testing comprises administering an active treatment to a first group, and administering a placebo to a second group and to a third group. Responders (i.e. those study participants who respond to either a treatment or a placebo) and non-responders (i.e. those study participants who do not respond to either a treatment or a placebo) are determined for each group. A second phase of testing is then performed. The second phase of testing comprises administering the placebo (or continuing the active treatment) to non-responders in the first group, administering the active treatment to non-responders to placebo in the second group, and continuing to administer the placebo to non-responders in the third group. The data from the first phase of testing and from the second phase of testing are analyzed to estimate the response rates to active treatment and to placebo. Since non-responders to placebo treatment in the first phase are used in the second phase, their placebo response in the second phase is likely to be reduced.

A system for performing a clinical trial having a reduced placebo effect is also presented. The system includes means for establishing a pool of eligible study participants, means for establishing a pool of enrolled and randomized study participants, means for identifying a pool of study participants completing a first phase of the study, means for identifying a pool of study participants for use in a second phase of the study, means for identifying a pool of study participants completing the second phase of the study, and means for generating data based on each phase of the study and means for analyzing the data. The first pool of enrolled and randomized study participants is used to enroll and randomize eligible study participants who agree to be randomized into one of three groups: a treatment group/arm, a first placebo group/arm and a second placebo group/arm. The first phase of the study administers active treatment to the first group/arm and placebo to the second and third groups/arms. After completion of the first phase of the study, the groups are separated into responders and non-responders. The non-responders to active treatment enter a second phase of the study where they are typically administered placebo or continue active treatment (to maintain the blinding during the second phase of the study). The non-responders to placebo during the first phase of the study will receive active treatment during the second phase of the study (in the case of second group/arm) or will continue to receive placebo during the second phase of the study (in the case of the third group/arm). Alternatively, patients may be randomized to drug or placebo during the first phase, and non-responders to placebo during the first phase are re-randomized to drug or placebo during the second phase. The resultant data from the first phase of the study and the second phase of the study are processed through a set of data analysis in order to determine the overall effectiveness of the active treatment(s) compared to placebo.

BRIEF DESCRIPTION OF THE DRAWINGS

The foregoing features of this invention, as well as the invention itself, may be more fully understood from the following description of the drawings in which.

DETAILED DESCRIPTION OF THE INVENTION

Before turning to the figures, it may first be helpful to provide a general overview and define some terminology. The present invention comprises a system and technique for implementing a study and a related analytical plan aimed at reducing both an overall placebo response rate and a sample size requirement for clinical trials. By reducing the placebo response rate and the sample size, the present invention can, among other things, lower the expense and time required to evaluate the efficacy of new therapeutic compounds.

The technique of the present invention utilizes two phases of treatment. The first phase involves a so-called "unbalanced randomization" between a placebo treatment group/arm and one or more active treatment(s) group(s)/arm(s). In such an unbalanced randomization, a greater number of study participants are randomly placed in a treatment group/arm where they will receive a placebo treatment rather than an active treatment. Thus, more study participants are said to be "randomized to placebo" than are "randomized to active treatment(s)" hence the term "unbalanced."

At the end of the first phase, so-called "responders" (i.e. those study participants who are given the active treatment and who respond to the active treatment as well as those study participants who are given the placebo and respond to the placebo) and non-responders (i.e. those study participants who are given the active treatment and who do not respond to the treatment as well as those study participants who are given the placebo and who do not respond to the placebo) are identified. For the purpose of the related analytical plan, only the data from the first phase of the study will be considered for the responders. However, responders to active treatment in the first phase may go on to continue the assigned double-blind treatment or may go on to open continuation treatment or may simply stop treatment.

In the second phase, non-responders treated with placebo in the first phase are randomized to either active treatment (or treatments) or placebo. Since study participants in the second phase have already not responded to a placebo treatment during the first phase, the number of responders to placebo treatment in the second phase will be substantially reduced. That is, on a percentage basis, fewer study participants will respond to the placebo in the second phase than responded in the first phase. The detailed study design, referred to as Sequential Parallel Comparison Design (SPCD) is represented by the block diagrams of FIGS. 1A and 1B and the flow diagram of FIG. 2. The analytical plan of the SPCD pools the data from both phases (with all the randomized study participants from the first phase and with all placebo non-responders during the first phase in the second phase) to increase the effectiveness of the analysis and reduce the required sample size.

Figure 1A:
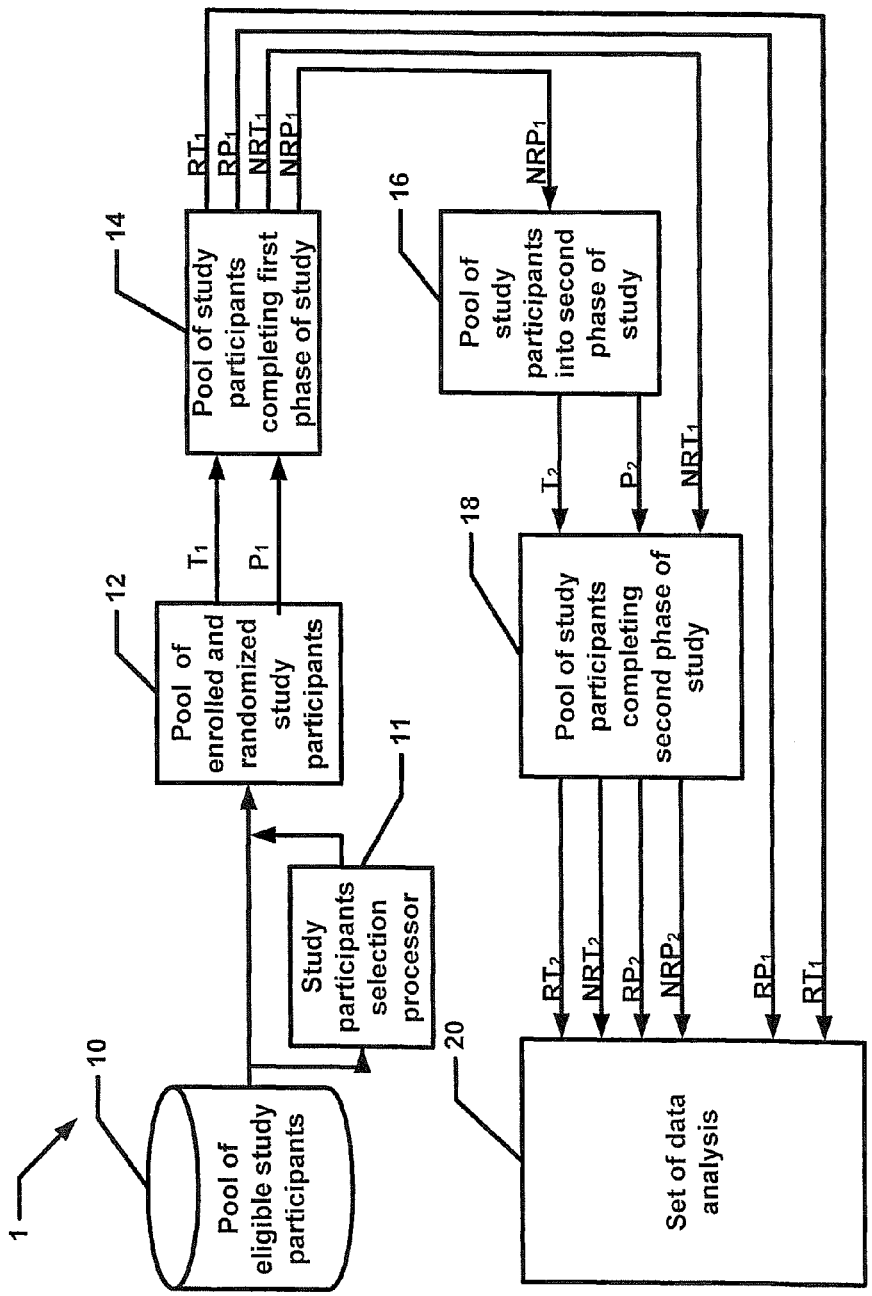
FIG. 1A is a block diagram of a system for designing and/or implementing a study having reduced placebo effect.

Referring now to FIG. 1A, a block diagram of a system 1 implementing a clinical drug study (or trial) utilizing the techniques of the present invention includes a pool of study participants 10 who are eligible to participate in the clinical trial. The pool of eligible study participants 10 may include subjects who are deemed to be appropriate for the study (based on clinical and sociodemographic characteristics) and may possibly participate in the study. As is generally known, such possible study participant characteristics of interest are those characteristics which are relevant or important to the clinical trial being designed. It should be appreciated that those of ordinary skill in the art of clinical trial design will know how to select such characteristics. Information relevant to the study as well as information on the pool of eligible study participants may be stored in a storage device such as a database, for example.

A study participants selection processor 11, coupled to the pool of eligible study participants 10 analyzes study participant characteristics and determines their appropriateness for inclusion in a particular clinical trial. Once selected, the pool of enrolled and randomized study participants 12 will include eligible study participants (e.g., having characteristics meeting certain prespecified criteria) who are identified and selected to participate in the clinical trial, who agree to participate in the study and be randomized as part of the study. It should be appreciated that the analysis performed to identify and select study participants may be done by a person with or without the aid of a processor such as a subject selection processor.

Once the study participants in the clinical drug trial are enrolled, the enrolled study participants are randomly placed into two groups. One group will receive active treatment and is designated $T_1$. The remaining group will receive placebo and is designated as $P_1$.

A first phase of the study 14 is then conducted on both groups. The duration of the first phase of the study will vary according to the condition under investigation and must allow enough time for the active treatment to show a difference compared with the placebo. The pool of study participants completing the first phase of study 14 are arranged into four groups. A first group is designated $RT_1$ and comprises study participants who showed a response to active treatment. A second group is designated $RP_1$ and comprises study participants who showed a response to placebo. Both the $RT_1$ group and the $RP_1$ group are excluded from the analytical aspect of the second phase of the study, although they may continue treatment as an extension of the double-blind treatment assignment or through an open treatment. A third group is designated $NRT_1$ and comprises study participants who did not show a response (non-responders) to active treatment. This group is included in the second phase of the study, although the data collected during the second phase of the study are not included in the analyses. The $NRT_1$ group may continue to receive active treatment during the second phase of the study or may go on placebo during the second phase of the study (in order to maintain the blinding). A fourth group, designated $NRP_1$, comprises study participants who did not show a response to placebo.

The $NRP_1$ group is provided to the pool of study participants into the second phase of the study 16. A randomization process is performed on this group 16 in order to randomly assign members of the $NRP_1$ group into a first treatment group/arm called $T_2$ where they will receive active treatment during the second phase of the study, and a second group/arm designated as $P_2$ where they will receive placebo during the second phase of the study.

The pool of study participants completing the second phase of study 18 results from the second phase of the study which is similar to the first phase of the study, and will typically include the same treatment(s) and placebo and have the same duration.

The pool of study participants completing the second phase of the study 18 are arranged into four groups. A first group, designated $RT_2$, comprises study participants who showed a response to active treatment. A second group, designated $NRT_2$, comprises study participants who did not show a response to active treatment. A third group, designated $RP_2$, comprises study participants who showed a response to placebo. A fourth group, designated $NRP_2$ comprises study participants who did not show a response to placebo.

The data are then analyzed through a set of data analysis 20 to provide clinical trial results. This may, for example, be accomplished in a data analyzer. The analysis 20 utilizes data from the $RP_1$, $RT_1$, $NRP_1$, $NRT_1$, $NRP_2$, $RP_2$, $NRT_2$ and $RT_2$ groups. Thus data from both the first and second phases of the study are analyzed to provide the clinical trial results.

It should be appreciated that in some embodiments or applications, it may be desirable to use more than two study phases and to arrange the participants into more than four discrete groups.

Figure 1B:
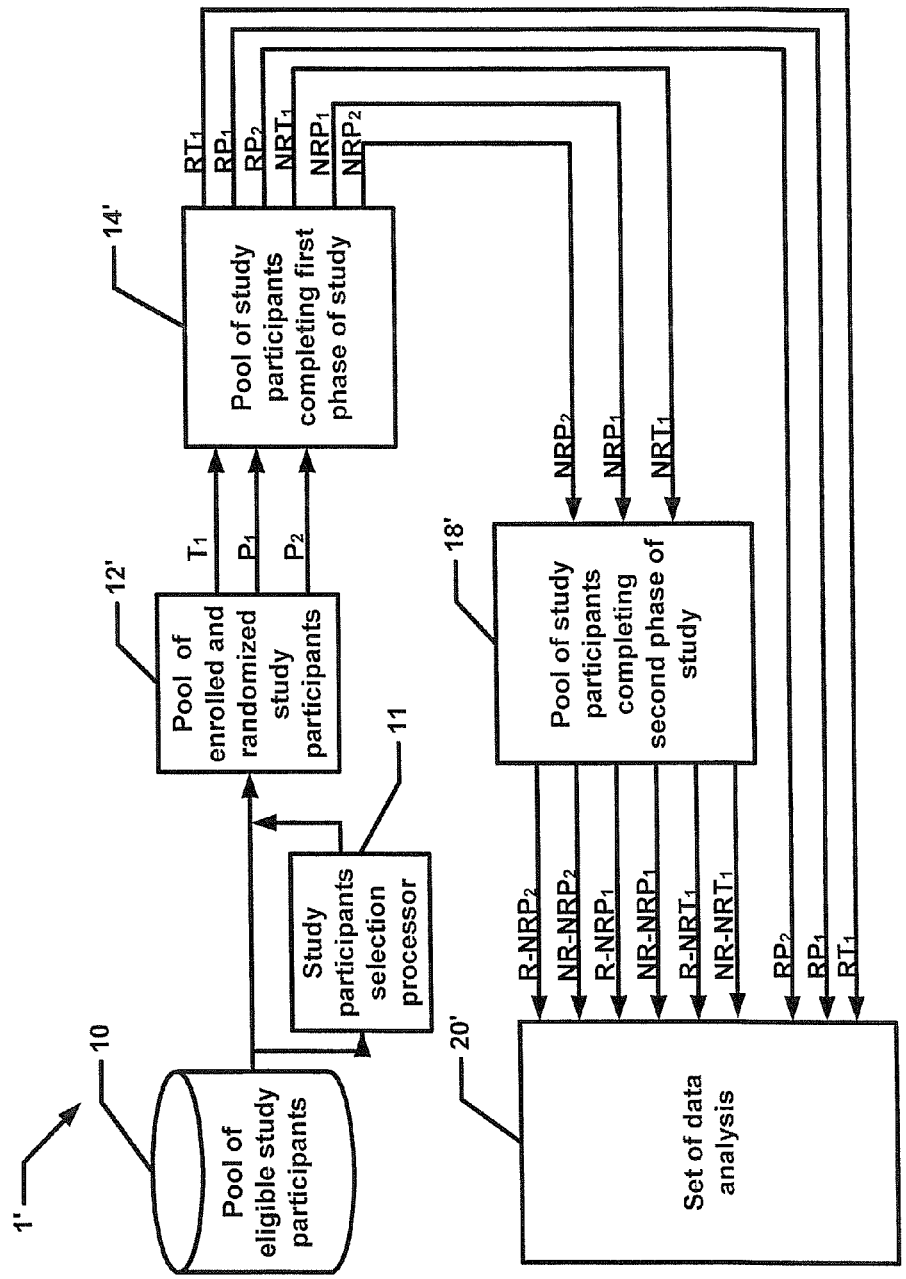
FIG. 1B is a block diagram of an embodiment of a system for designing and/or implementing a study using the techniques of the present invention.

Referring now to FIG. 1B, a block diagram of a second system 1' implementing a clinical drug study utilizing the techniques of the present invention includes a pool of study participants 10 who are eligible to participate in the clinical trial. The pool of eligible study participants 10 may include subjects who are deemed to be appropriate for the study (based on clinical and socio-demographic characteristics) and may possibly participate in the study. As is generally known, such possible study participant characteristics of interest are those characteristics which are relevant or important to the clinical trial being designed. It should be appreciated that those of ordinary skill in the art of clinical trial design will know how to select such characteristics.

A study participants selection processor 11, coupled with the pool of eligible study participants 10 analyzes study participant characteristics and determines their appropriateness for inclusion. Once selected, the pool of enrolled and randomized study participants 12' will include eligible study participants (e.g., having characteristics meeting certain prespecified criteria) who are identified and selected to participate in the clinical trial, who agree to participate in the study and be randomized as part of the study. It should be appreciated that the analysis performed to identify and select study participants may be done by a person with or without the aid of a processor such as a subject selection processor.

Once the study participants in the clinical drug trial are enrolled, the enrolled study participants are randomly placed into three groups. One group will receive active treatment and is designated $T_1$. The remaining two groups will receive placebo and are designated together as $P_1$ and $P_2$.

A first phase of the study is then conducted on all three groups. The duration of the first phase of the study will vary according to the condition under investigation and must allow enough time for the active treatment to show a difference against placebo. The pool of study participants completing the first phase of study 14' are arranged into six groups. A first group is designated $RT_1$ and comprises study participants who showed a response to active treatment. A second group is designated $RP_1$ and comprises study participants who showed a response to the first placebo group/arm. A third group is designated $RP_2$ and comprises study participants who showed a response to the second placebo group/arm (typically the same as the first placebo). The $RT_1$ group, $RP_1$ group and the $RP_2$ group are excluded from the analytical aspect of the second phase of the study, although they may continue treatment as an extension of the double-blind treatment assignment or through an open treatment. A fourth group is designated $NRT_1$ and comprises study participants who did not show a response (non-responders) to active treatment. A fifth group, designated $NRP_1$, comprises study participants who did not show a response to the first placebo group/arm. A sixth group, designated $NRP_2$, comprises study participants who did not show a response to the second placebo group/arm.

The $NRT_1$ group, $NRP_1$ group and $NRP_2$ group are used to form the pool of study participants completing the second phase of study 18 which results from the second phase of the study which is similar to the first phase of the study, and will typically include the same treatment and placebo and have the same duration. The $NRP_1$ group will receive active treatment during the second phase of the study, the $NRP_2$ group will continue to receive placebo during the second phase of the study. The $NRT_1$ group may continue to receive active treatment during the second phase of the study or may go on placebo during the second phase of the study (in order to maintain the blinding), although the data collected during the second phase of the study are not included in the analyses.

The pool of study participants who complete the second phase of the study are arranged into six groups. A first group, designated $R\text{-}NRP_2$, corresponds to those study participants who did not respond to placebo in the first phase of the study but showed a response to placebo in the second phase of the study. A second group, designated $NR\text{-}NRP_2$, corresponds to those study participants who did not respond to placebo in the first phase of the study and did not show a response to placebo in the second phase of the study as well. A third group, designated $R\text{-}NRP_1$, corresponds to those study participants who did not respond to placebo in the first phase of the study but showed a response to active treatment in the second phase of the study. A fourth group, designated $NR\text{-}NRP_1$, corresponds to those study participants who did not respond to placebo in the first phase of the study and who did not show a response to active treatment in the second phase of the study. A fifth group, designated $R\text{-}NRT_1$, corresponds to those study participants who did not respond to active treatment in the first phase of the study but showed a response to active treatment (or placebo) in the second phase of the study. A sixth group, designated $NR\text{-}NRT_1$, corresponds to those study participants who did not respond to active treatment in the first phase of the study and did not show a response to active treatment (or placebo) in the second phase of the study.

The data are then analyzed using a set of data analysis tools 20'. The analysis 20' utilizes data from the $RP_1$, $RT_1$, $RP_2$, $NRP_1$, $NRT_1$, $NRP_2$, $R\text{-}NRP_2$, $NR\text{-}NRP_2$, $R\text{-}NRP_1$, and $NR\text{-}NRP_1$, groups. Thus data from both phases of the study are analyzed to provide the clinical drug trial results and to compare the effects of the active treatment(s) and placebo.

Figure 2:
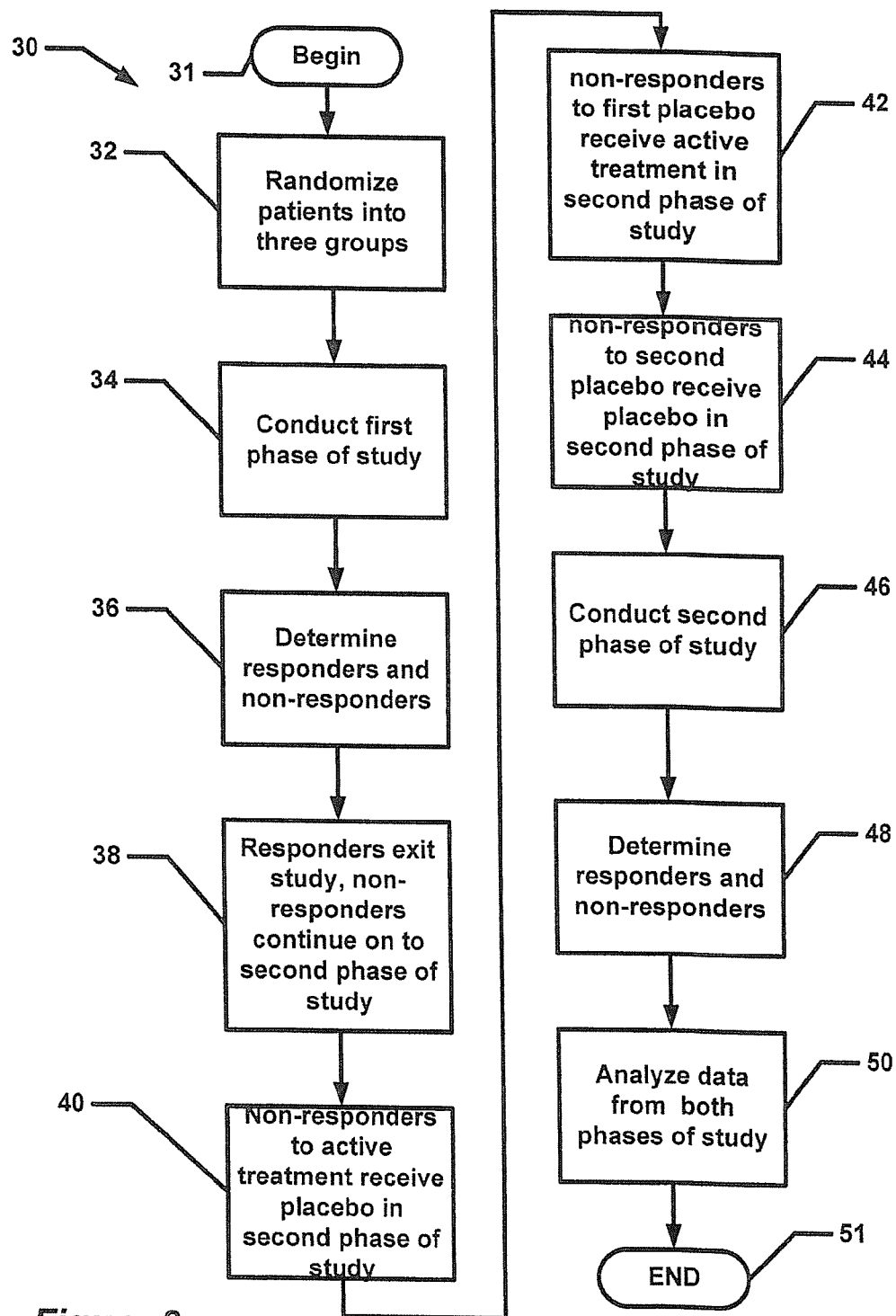
FIG. 2 is a flow diagram which describes a process to design and/or perform a clinical trial having a reduced placebo effect.

A flow diagram of the presently disclosed method is depicted in FIG. 2. The rectangular shaped elements are herein denoted "processing blocks" and the diamond shaped elements, are herein denoted "decision blocks." It should be appreciated that all, some or none of the functions provided in each of the processing and decision blocks may be carried out by humans or may be carried out by processors. Thus in one embodiment, the "processing blocks" represent computer software instructions or groups of instructions and the "decision blocks" represent computer software instructions, or groups of instructions which affect the execution of the computer software instructions represented by the processing blocks. It should be noted that the flow diagram of FIG. 2 represents one embodiment of the design and variations in such a flow diagram which generally follow the process outlined above and are considered to be within the scope of the present invention.

Alternatively, the processing and decision blocks represent processes which can be performed by functionally equivalent circuits such as a digital signal processor circuit or an application specific integrated circuit (ASIC). The flow diagrams do not depict the syntax of any particular programming language. Rather, the flow diagrams illustrate the functional information one of ordinary skill in the medical field requires to perform the functions/processes in accordance with the present invention. It should be noted that many routine program elements, such as initialization of loops and variables and the use of temporary variables are not shown. It will be appreciated by those of ordinary skill in the medical field that unless otherwise indicated herein, the particular sequence of steps described is illustrative only and can be varied without departing from the spirit of the invention. Thus, unless otherwise stated the processes described below are unordered meaning that, when possible, the processes can be performed in any convenient or desirable order.

Referring now to FIG. 2, a flow diagram showing the SPCD methodology 30 for performing a clinical trial is shown. Before describing the steps in detail, it should be appreciated that a clinical trial designed and/or implemented in accordance with the present invention is conducted in at least two phases and the phases can be of equal duration. While in some clinical trials it is preferable to have the duration of each phase be the same, it should be appreciated that in the present technique, each phase may have a different duration. It should also be appreciated that in some clinical trials, the duration of each phase is shorter than that of standard clinical trials and capitalizes on the observation that drug-placebo differences can be detected relatively early in the clinical trial. There may, however, be some instances when the duration of each phase is the same as or even larger than that of standard clinical trials. The particular duration of each phase of the clinical trial is selected in accordance with a variety of factors including (but not limited to) the type of disorder under investigation, the natural course of the disorder, the estimated placebo response rate, and the estimated proportion of study participants continuing into the second (or later) phase of the study.

It should be appreciated that in some cases a trade-off must be made between lowering the placebo response rate and exposing the study participants to the treatment. For example, a drug company may want as many people as possible to be exposed to a particular active drug treatment. The design will reflect such considerations.

Turning now to FIG. 2, processing begins in processing block 32 in which, after an initial screening visit, eligible study participants are randomly allocated to one of three possible treatment groups: drug alone (DP), placebo then drug (PD) and placebo then placebo (PP). The allocation is done in an unbalanced ratio. One possibility is using a 2:3:3 ratio (DP:PD:PP) in blocks of 8 to maintain the 2:3:3 ratio between groups. However, in general, the ratio could be 1-2a, a,a for a choice of "a" (in units of percent %) to maximize power (see examples discussed below in conjunction with FIGS. 3 and 4).

It should be appreciated that in a preferred embodiment, the same number of study participants are included in the placebo-drug (PD) and the placebo-placebo (PP) treatment groups. If a 2:3:3 ratio is used during the first phase of the trial, 75% (or 2a) of the study participants are randomized to placebo and 25% (or 1-2a) are randomized to active treatment. The specific ratio used can be of any values, with several factors leading to selection of a particular ratio. A ratio which results in potential study participants having a relatively high overall chance (e.g., 50%) for assignment to active treatment is typically preferred by study participants. The 2:3:3 ratio yields approximately a 50% chance of a study participant being assigned to active treatment. In general, however, any ratio which results in more non-responders to placebo for phase two of the study is more informative as data comes from phase two of the study as well.

Processing block 34 recites that the first phase of the study is performed. This includes administering the active treatment to the DP group and administering placebo to the PD group and to the PP group.

Processing block 36 discloses that at the end of the first phase of the study, a study clinician or administrator determines whether each participant is a responder or a non-responder. That is, responders and non-responders for the DP group, responders and non-responders for the PD group, and responders and non-responders for the PP group are determined.

Processing block 38 recites that the responders for each of the groups exit the double-blind study (from a data analysis perspective). These responders can continue double-blind treatment, enter an open-label continuation therapy, follow-up, or simply discontinue their double-blind treatment. Non-responders for each group at the end of the first phase of the study participate in a second phase of similar duration. It should be appreciated that in the second phase of the study, the placebo will be administered in a double-blind fashion.

Next, as shown in processing block 40, those study participants in the first phase who were non-responders to the active treatment receive placebo (or may continue to receive active treatment) in the second phase of the study (so that we do not unblind study participants and investigators).

Next as shown in processing block 42, those study participants in the first phase who were part of the first group/arm to receive placebo and who were non-responders to the first placebo receive active treatment in the second phase of the study. The active treatment will be administered in a double-blind fashion as part of the second phase of the study.

In processing block 44, those study participants in the first phase who were part of the second group/arm to receive placebo and who were non-responders to the placebo receive placebo again in the second phase of the study. Similar to the other groups in the second phase of the study, the placebo will be administered in a double-blind fashion.

The second phase of the study begins in processing block 46. Since those study participants in the second phase have already failed to respond to placebo in the first phase (i.e. they have already "failed placebo,") their placebo response will be reduced.

As shown in processing block 48, at the end of the second phase of the study, the study clinician or administrator determines whether each participant is a responder or a non-responder. That is, responders and non-responders in each of the three groups, are determined.

As shown in processing block 50, the data from both phases are pooled and analyzed. By pooling the data, it is possible to maximize power and reduce the required sample size. The response rates of the first phase of testing are pooled with the response rates of the second phase (for the placebo non-responders during the first phase only), therefore the response of each patient is counted twice, which results in a smaller sample size being required to achieve a requisite power for the study. Processing then ends as shown in processing block 51.

In one embodiment, the effect of the active treatment is assessed using a z-score, which has a normal distribution with a standard deviation of 1. The z-score is computed by pooling the data from all three treatment groups and using a pooling ratio to maximize power. Under the null hypothesis of no drug placebo difference, the z-score will have a mean value of zero. In this way, all the data from the first and second phases of the study is used in the analysis allowing for a smaller sample size (i.e. higher power). It should be noted that data from the study participants who failed active treatment in the first phase of the study (DP group) and who are exposed to placebo during the second phase of the study is not used to calculate the placebo response rate. Similarly, in the event that subjects that fail active treatment in the first phase are kept on active treatment during the second phase, their responses are not counted as part of the analysis.

While the present description involves the comparison of one active treatment and placebo without an active comparator, it should be understood that a version of this design could be developed for trials with multiple active comparators.

Figure 3:
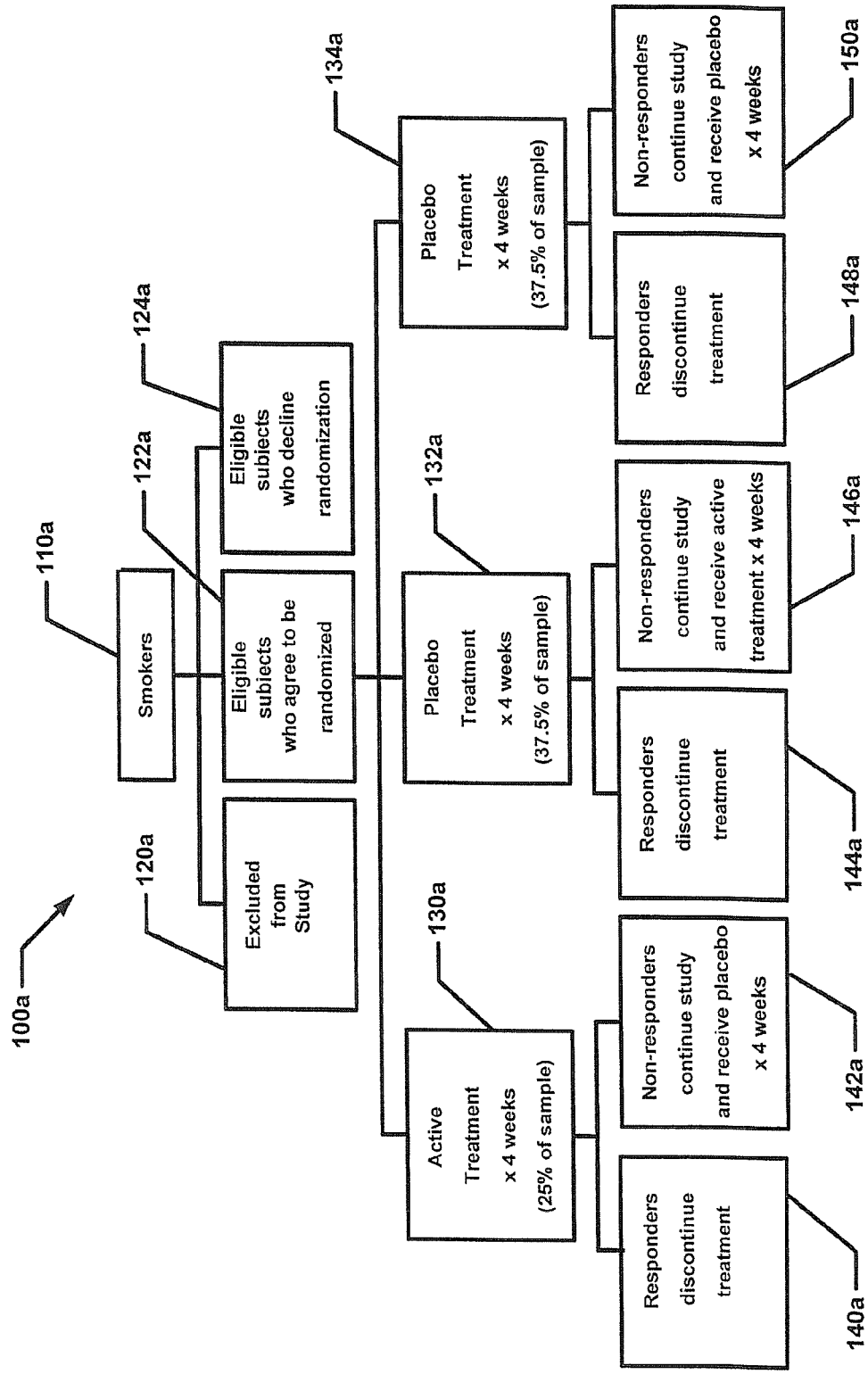
FIG. 3 is a block diagram of a first study example.

Referring now to FIG. 3, a diagrammatic representation illustrates the phases and organization of a planned smoking cessation study arrived at using the above-described methodology to design a clinical study.

As shown in FIG. 3, a group of subject smokers 110a are divided into three possible groupings as follows: (1) those who are excluded from the study 120a; (2) those who are eligible to participate in the study and who agree to be randomized 122a; and (3) those who are eligible to participate in the study but who decline to be randomized 124a. The eligible study participants who agree to be randomized (i.e. group 122a) are randomized into three groups identified as 130a, 132a, and 134a in FIG. 3. This selection process is referred to as the subject selection phase.

Next, in phase one of the study, a first group 130a receives active treatment. In this particular example, where the eligible study participants are smokers, they receive the active treatment for four weeks. The particular length of time of any study depends upon a variety of factors well known to those of ordinary skill in the medical field.

A second group 132a receives placebo for the same duration of time in which group 130a which receives the active treatment (i.e. study participants in group 130a receive the active treatment for 4 weeks and study participants in group 132a receive the placebo treatment for 4 weeks).

Similar to the second group, a third group 134a also receives placebo for the same duration of time as the first group 130a and the second group 132a.

Once the first phase of treatment has been completed, the study participants in each of the groups 130a, 132a, 134a are separated into responders and non-responders. In group 130a, those study participants who quit smoking are considered responders (specifically, responders to treatment) and those study participants who do not quit smoking are considered non-responders (specifically, non-responders to treatment). Similarly, in groups 132a, 134a, those study participants who quit smoking are identified as responders (specifically, responders to placebo) while those study participants who do not quit smoking are identified as non-responders (specifically, non-responders to placebo).

After the responders and non-responders are identified, phase two of the study begins. For the active treatment group 130a, responders 140a discontinue further treatment. Non-responders 142a, on the other hand, continue the study and receive placebo for the duration of phase two (which, in this particular example, is another four week phase).

The first placebo group responders 144a discontinue further treatment, while the first placebo group non-responders 146a continue the study and receive active treatment for the duration of phase two of the study.

The second placebo group responders 148a discontinue further treatment, while the second placebo group non-responders 150a continue the study and receive placebo for the duration of phase two of the study. In an alternate embodiment the first and second placebo group non-responders are grouped together during phase 1 and then randomized into a group that will receive active treatment and a group that will receive placebo during the second phase of the study.

After the second phase is completed, the data from both the first and second phases of the study are analyzed to determine the effectiveness of the active treatment(s) compared to placebo. One exemplary analysis is described next. While a preferred method of performing the analysis is described below, it should be appreciated that other methods of performing analysis of the data are also within the scope of the present invention.

In the below analysis of the data from the smoking cessation study, it is assumed that study participants will have an initial response rate of 45% on drug and 25% on placebo. It is further assumed that the non-responders to placebo will have a response rate of 25% on drug and 10% on placebo. These assumptions are based on prior studies in the field of smoking cessation research.

Using the SPCD methodology, 172 study participants would be needed to achieve 90% power based on the well-known asymptotic formula. The value of a (i.e. the randomization fraction) in this case would be 27.5%. That is 55% would be initially randomized to placebo and 45% to active treatment in the first phase. This could be accomplished by randomizing the first block of study participants to the three treatment groups (DP, PP, PD) at ratios of 9:5:6, the second group at 9:6:5, repeating this pattern for the next 6 groups and randomizing the last group at ratios of 3:3:5.

If 75% are randomized initially to placebo (with a 2:3:3 ratio of DP:PD:PP in blocks of 8) and 25% to active treatment, the power is 87% based on the well-known asymptotic formula.

If a conventional technique having only one period and equal randomization were used to design the study, the power would be 80% based upon the asymptotic formula. To achieve the same power value (i.e. the 90% power value achieved using the SPCD technique) it would be necessary to use 260 study participants (vs. the 172 study participants used to achieve 90% power value using the SPCD technique).

The power was also calculated by simulation of 5,000 clinical trials. The simulation results were used to provide calculations; in that case the corresponding power values were 94% and 87%.

If the estimates of the placebo response rate turn out to be overly conservative, the 55% random allocation to placebo may yield too few study participants to enter the second phase. For this reason, it may be preferable to use the 75% random allocation to placebo as shown in FIG. 3.

It should be noted that in the example of FIG. 3, the proportions randomized to the three groups are done so in a ratio 1-2a:a:a. The response rates to the first administration of drug and placebo can be denoted as $p_1$, $q_1$ respectively and the drug and placebo response rates to the second treatment can be denoted as $p_2$, $q_2$ respectively.

In one embodiment, the data analysis involves computing a value h representative of the effectiveness of the treatment. The effectiveness of the treatment, h, may be computed as:

$$h = w(p_1 - q_1) + (1-w)(p_2 - q_2)$$

in which:
w=a weighting factor

The weighting factor, w and the randomization fraction a are chosen to maximize the power of the test, based on the alternative hypothesis.

Computation of the standard error for the effectiveness value h requires consideration of the fact that some of the same study participants who are included in the estimation of $p_2$, $q_2$ are also included in the estimation of $p_1$, $q_1$. The delta method was used to compute the standard error of the value of the effectiveness of the treatment h. The computation is facilitated by considering the following table of outcomes, where in this case the response rates to the first administration of drug and placebo $p_1$, $q_1$ and the response rates to the second administration of drug and placebo $p_2$, $q_2$ are the theoretical probabilities (rather than the observed relative frequencies).

| Group | Response | Frequency | Probability |
| --- | --- | --- | --- |
| 1-Placebo-Placebo | No-Yes | $n_{1,1}$ | $(1 - q_1) * q_2$ |
|  | No-No | $n_{1,2}$ | $(1 - q_1) * (1 - q_2)$ |
|  | Yes | $n_{1,3}$ | $q_1$ |
| 2-Placebo-Drug | No-Yes | $n_{2,1}$ | $(1 - q_1) * p_2$ |
|  | No-No | $n_{2,2}$ | $(1 - q_1) * (1 - p_2)$ |
|  | Yes | $n_{2,3}$ | $q_1$ |
| 3-Drug | Yes | $n_{3,1}$ | $p_1$ |
| (this is the drug-placebo group, but the data from phase 2 on placebo are not considered in the analyses) | No | $n_{3,2}$ | $1 - p_1$ |

Then, the effectiveness value, h, may be computed as:

$$h = w\left(\frac{n_{3,1}}{n(1-2a)} - \frac{(n_{1,3} + n_{2,3})}{2na}\right) + (1-w)\left(\frac{n_{2,1}}{n_{2,1} + n_{2,2}} - \frac{n_{1,1}}{n_{1,1} + n_{1,2}}\right),$$

in which:
n is the total number of study participants;
$n_{1,1}$ is the number of participants who were non-responders to placebo in the first phase and were responders to placebo in the second phase;
$n_{1,2}$ is the number of participants who were non-responders to placebo in the first phase and were non-responders to placebo in the second phase;
$n_{1,3}$ is the number of participants who were responders to placebo in the first phase and were responders to placebo in the second phase;
$n_{2,1}$ is the number of participants who were non-responders to placebo in the first phase and were responders to treatment in the second phase;
$n_{2,2}$ is the number of participants who were non-responders to placebo in the first phase and were non-responders to treatment in the second phase;
$n_{2,3}$ is the number of participants who were responders to placebo in the first phase and were responders to treatment in the second phase;
$n_{3,1}$ is the number of participants who were responders to treatment in the first phase;

w is a weighting factor; and
a is a randomization fraction.

The standard error of h (denoted as $h_{standard\ error}$) can be computed as:

$$h_{standard\ error} = \sqrt{D'VD}$$

in which:
D is the column vector of derivatives of h with respect to $n_{3,1}$, $n_{1,3}$, $n_{2,3}$, $n_{2,1}$, $n_{2,2}$, $n_{1,1}$, $n_{1,2}$;
D' is the transpose of D; and
V is the variance covariance matrix of $n_{3,1}$, $n_{1,3}$, $n_{2,3}$, $n_{2,1}$, $n_{2,2}$, $n_{1,1}$, $n_{1,2}$ from the multinomial distribution.

It should be appreciated that the standard error of h, $h_{standard\ error}$, is computed with the observed values of $p_1$, $p_2$, $q_1$, $q_2$.

The formula below is a simplified calculation of the standard error of h.

$$\sqrt{\frac{\begin{array}{c}-2(-1+2a)p_2(-1+w)^2 + 2(-1+2a)p_2^2(-1+w)^2 - \\ 2(-1+2a)q_2(-1+w)^2 + 2(-1+2a)q_2^2(-1+w)^2 + \\ (-1+q_1)((-1+q_1)q_1 + 2a(-p_1 + p_1^2 + q_1 - q_1^2))w^2\end{array}}{2a(-1+2a)n(-1+q_1)}}$$

To test the null hypothesis z=h/s was used. The values of a and w were calculated by substituting the alternative hypothetical values of $p_1$, $p_2$, $q_1$, $q_2$ and finding the values of a and w that maximize z. The power of the test is then $\Phi$ (z−1.96) where $\Phi$ is the cumulative distribution of the normal distribution.

Figure 4:
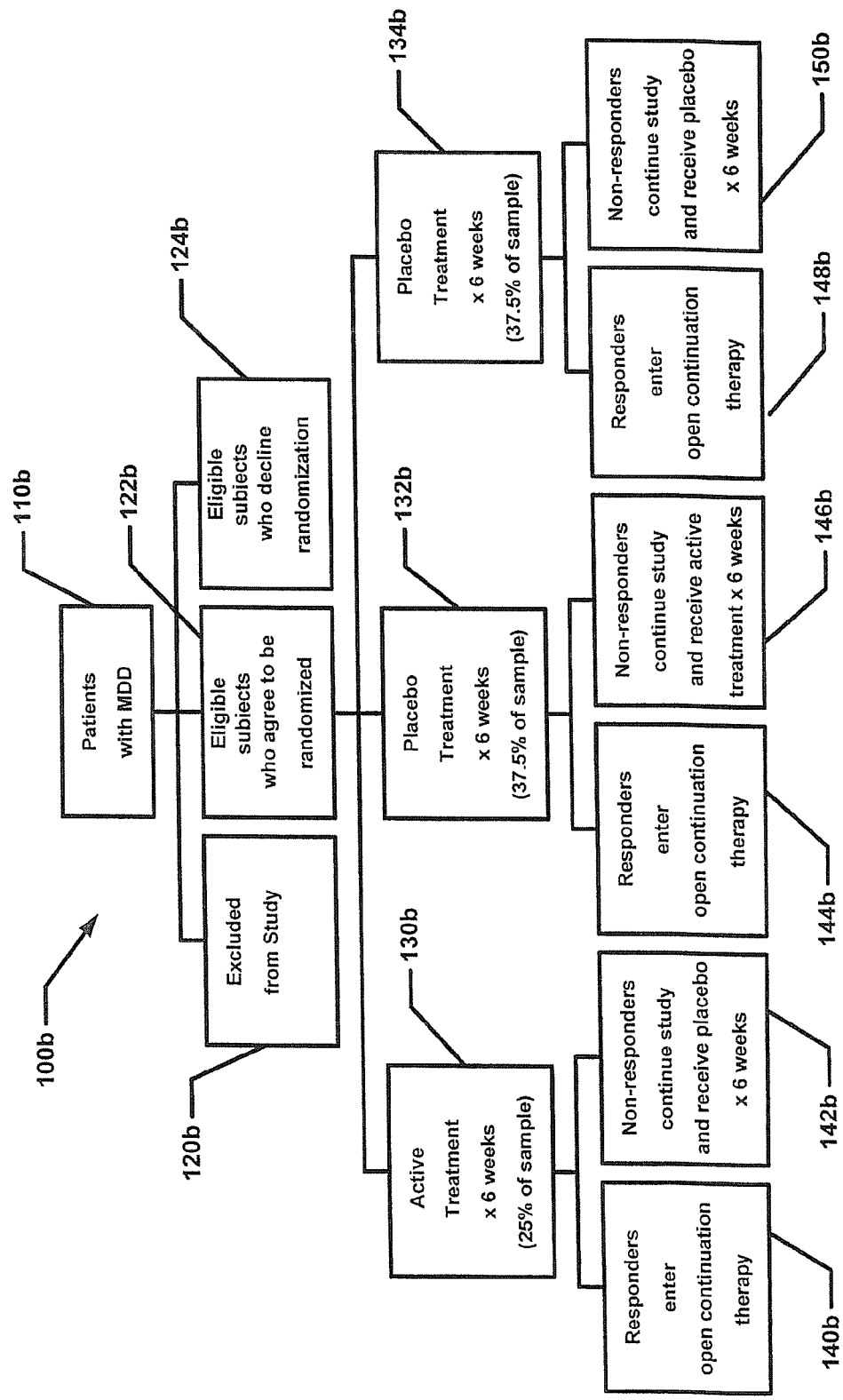
FIG. 4 is a block diagram of a second study example.

FIG. 4 is a schematic representation of another example of the SPCD methodology applied to a population with major depressive disorder (MDD).

Referring now to FIG. 4, a diagrammatic representation illustrates the phases and organization of a planned MDD treatment study arrived at using the above-described clinical study design methodology.

As shown in FIG. 4, a group of selected study participants 110*b* are divided into three possible groupings as follows: (1) those who are excluded from the study 120*b*; (2) those who are eligible and who agree to be randomized 122*b*; and (3) those who are eligible study but who decline to be randomized 124*b*. The eligible study participants who agree to be randomized are randomized into three groups. This selection process is referred to as the subject selection phase.

Next, in the first phase of the study, a first group 130*b* receives active treatment. In this example, the eligible study participants receive an active treatment for six weeks. The particular length of time of any study depends upon a variety of factors well known to those of ordinary skill in the medical field.

A second group 132*b* receives placebo for the same duration of time as group 130*b* which receives the active treatment (i.e. study participants in group 132*b* receive the placebo treatment for six weeks).

Similar to the second group, a third group 134*b* also receives placebo for the same duration of time as the first group 130*b* and the second group 132*b*.

Once the first phase of treatment ends, the study participants in each of the groups 130*b*, 132*b*, 134*b* are separated into responders and non-responders. In group 130*b*, those study participants who show improvement are considered responders and those study participants who do not show improvement are considered non-responders. Similarly, in groups 132*b* and 134*b*, those study participants who show improvement are identified as responders while those study participants who do not show improvement are identified as non-responders.

After the responders and non-responders are identified, the second phase of the study begins. For the active treatment group 130b, responders 140b enter open continuation therapy. Non-responders 142b continue the study and receive placebo (or continue active treatment) for another six week phase.

The first placebo group responders 144b also enter open continuation therapy, while the first placebo group non-responders 146b continue the study and receive active treatment for another six week phase.

The second placebo group responders 148b enter open continuation therapy, while the second placebo group non-responders 150b continue the study and receive placebo for another six week phase.

After the second phase is completed, the data from both phases of the study are pooled and analyzed to determine the effectiveness of the treatment.

In summary, a method of performing a clinical drug trial with a reduced placebo effect has been described. In its typical embodiment, the method includes randomizing study participants into three treatment groups and performing a first phase of treatment testing on the three groups. The first phase of testing comprises administering an active treatment to a first group, and administering a placebo to a second group and to a third group. Responders and non-responders are determined for each group at the end of the first phase. A second phase of testing is then performed. The second phase of testing comprises administering placebo (or continuing active treatment) to non-responders in the first group, administering active treatment(s) to non-responders in the second group, and administering placebo to non-responders in the third group. The data from the first phase of testing and from the second phase of testing (for the placebo non-responders during the first phase only) are analyzed to provide the response rate to active treatment(s) and the response rate to placebo. Since study participants in the second phase of testing have already failed placebo during the first phase, their placebo response is reduced.

Having described preferred embodiments of the invention it will now become apparent to those of ordinary skill in the art that other embodiments incorporating these concepts may be used. Accordingly, it is submitted that the invention should not be limited to the described embodiments but rather should be limited only by the spirit and scope of the appended claims.

What is claimed is:

1. A method comprising:
    specifying, on an a priori basis, characteristics of a population of participants eligible to be included in a first phase of a clinical trial and characteristics of one or more subpopulations of participants of said population eligible to be included in a second phase of said clinical trial;
    identifying a group of potential participants for said first phase of said clinical trial as having said specified characteristics of said population;
    with respect to said first phase of said clinical trial:
        allocating two or more of said potential participants in said identified group into a first plurality of treatment groups comprising a first active treatment group of participants and a first placebo group of participants;
        administering at least one participant in said first active treatment group with at least an active treatment;
        administering at least one participant in said first placebo group with at least a placebo;
        analyzing first phase response data of one or more of said participants in said first active treatment group and said first placebo group for response; and
        identifying, based at least on said analyzing first phase response data, and on said characteristics of said one or more subpopulations, one or more groups of participants, each of which satisfies characteristics of at least one of said one or more subpopulations, to potentially be included in said second phase of said clinical trial;
    with respect to said second phase of said clinical trial:
        allocating one or more participants from each of said one or more groups identified to potentially be included in said second phase into a second plurality of treatment groups comprising at least a second active treatment group and a second placebo group;
        administering at least one participant in said second active treatment group with said at least an active treatment;
        administering at least one participant in said second placebo group with said at least a placebo;
    analyzing second phase response data of one or more of said participants in said second active treatment group and said second placebo group for response; and
    determining, using one or more processors, at least one measure of efficacy of said at least an active treatment, based at least in part on use of said analyzed first phase response data, use of said analyzed second phase response data, and use of an a priori null hypothesis,
    wherein said a priori null hypothesis is that:
        (a) no difference exists between response to said at least an active treatment and response to said at least a placebo in said population, and
        (b) no difference exists between response to said at least an active treatment and response to said at least a placebo in each of said one or more subpopulations.

2. A method as in claim 1, wherein determining, using said one or more processors, at least one measure of efficacy of said at least an active treatment, based at least in part on use of said analyzed first phase response data, use of said analyzed second phase response data, and use of said a priori null hypothesis, comprises utilizing response data of at least one participant at least twice, by including response data of such participant from said first phase and from said second phase.

3. A method as in claim 1, wherein identifying, based on said analyzing first phase response data, and on said characteristics of said one or more subpopulations, one or more participants, each of which satisfies characteristics of at least one of said one or more subpopulations, to potentially be included in said second phase of said clinical trial, comprises utilizing said first phase response data in order to determine if at least one participant in said first phase has the characteristics of at least one of said one or more subpopulations and is therefore eligible to be included in said second phase.

4. A method as in claim 1, wherein said at least an active treatment comprises at least one active comparator.

5. A method as in claim 1, wherein certain participants in said first phase also receive said at least an active treatment or said at least a placebo in said second phase but second phase response data of said certain participants are excluded from said analyzed second phase response data used in determining said at least one measure of efficacy.

6. A method as in claim 5, wherein said second phase response data of one or more of said certain participants are excluded from said analyzed second phase response data used in determining said at least one measure of efficacy based on a determination that said one or more of said certain participants fail to satisfy one or more characteristics of at least one of said one or more subpopulations.

7. A method of determining efficacy of at least an active treatment as compared to at least a placebo, based on data obtained during a clinical trial conducted according to at least the following: (a) specifying, on an a priori basis, characteristics of a population of participants eligible to be included in a first phase of a clinical trial and characteristics of one or more subpopulations of participants of said population eligible to be included in a second phase of said clinical trial; (b) identifying a group of potential participants for said first phase of said clinical trial as having said specified characteristics of said population; (c) with respect to said first phase of said clinical trial: (i) allocating two or more of said potential participants in said identified group into a first plurality of treatment groups comprising a first active treatment group of participants and a first placebo group of participants; (ii) administering at least one participant in said first active treatment group with at least an active treatment; (iii) administering at least one participant in said first placebo group with at least a placebo; (iv) analyzing first phase response data of one or more of said participants in said first active treatment group and said first placebo group for response; and (v) identifying, based at least on said analyzing first phase response data, and on said characteristics of said one or more subpopulations, one or more groups of participants, each of which satisfies characteristics of at least one of said one or more subpopulations, to potentially be included in said second phase of said clinical trial; (d) with respect to said second phase of said clinical trial: (i) allocating one or more participants from each of said one or more groups identified to potentially be included in said second phase into a second plurality of treatment groups comprising at least a second active treatment group and a second placebo group; (ii) administering at least one participant in said second active treatment group with said at least an active treatment; and (iii) administering at least one participant in said second placebo group with said at least a placebo; said method comprising:

analyzing second phase response data of one or more of said participants in said second active treatment group and said second placebo group for response; and determining, using one or more processors, at least one measure of efficacy of said at least an active treatment, based at least in part on use of said analyzed first phase response data, use of said analyzed second phase response data, and use of an a priori null hypothesis, wherein said a priori null hypothesis is that:
(a) no difference exists between response to said at least an active treatment and response to said at least a placebo in said population, and
(b) no difference exists between response to said at least an active treatment and response to said at least a placebo in each of said one or more subpopulations.

8. A non-transitory computer readable medium storing software that performs the method of claim 7.

* * * * *

UNITED STATES PATENT AND TRADEMARK OFFICE
CERTIFICATE OF CORRECTION

PATENT NO. : 8,219,419 B1
APPLICATION NO. : 13/403060
DATED : July 10, 2012
INVENTOR(S) : Maurizio Fava et al.

Page 1 of 1

It is certified that error appears in the above-identified patent and that said Letters Patent is hereby corrected as shown below:

In the Specification

Col. 1, line 8, delete "application of U.S." and replace with --application of co-pending U.S.--

Signed and Sealed this
Twenty-fourth Day of March, 2015

Michelle K. Lee
*Director of the United States Patent and Trademark Office*